US005635159A

United States Patent [19]
Fu Lu et al.

[11] Patent Number: 5,635,159
[45] Date of Patent: Jun. 3, 1997

[54] AEROSOL DRUG FORMULATIONS CONTAINING POLYGLYCOLYZED GLYCERIDES

[75] Inventors: Mou-Ying Fu Lu, Lake Bluff; Akwete L. Adjei, Wadsworth; Pramod K. Gupta, Gurnee, all of Ill.

[73] Assignee: Abbott Laboratories, Abbott Park, Ill.

[21] Appl. No.: 296,778

[22] Filed: Aug. 26, 1994

[51] Int. Cl.$^6$ ................................... A61K 9/12
[52] U.S. Cl. ........................... 424/45; 424/46
[58] Field of Search ........................ 424/43, 45, 46

[56] References Cited

U.S. PATENT DOCUMENTS

| | | | |
|---|---|---|---|
| 4,851,211 | 7/1989 | Adjei et al. | 424/45 |
| 4,897,256 | 1/1990 | Adjei et al. | 424/43 |

FOREIGN PATENT DOCUMENTS

| | | | |
|---|---|---|---|
| 0510731 | 10/1992 | European Pat. Off. | 424/45 |
| 518600 | 12/1992 | European Pat. Off. | |
| 518601 | 12/1992 | European Pat. Off. | |
| 561166 | 9/1993 | European Pat. Off. | |
| 93/18746 | 9/1993 | WIPO | |

*Primary Examiner*—Raj Bawa
*Attorney, Agent, or Firm*—Mona Anand

[57] ABSTRACT

Pharmaceutical compositions for aerosol delivery comprising (a) a medicament, (b) a non-chlorofluorocarbon propellant, and (c) a polyglycolized glyceride having a hydrophilic lipophilic balance of between and including 6 and 14, wherein the medicament is present in a concentration of between about 0.05% and about 5% by weight and the polyglycolized glyceride is present in a concentration of between about 0.001% and about 10% by weight, the nonchlorofluorocarbon propellant is selected from the group consisting of HCFC 123, HCFC 124, HCFC 141b, HCFC 225, HCFC 125, FC-C 51-12, DYMEL A, DYMEL 152a, HFC 134a and HFC 227ea in which unwanted aggregation of the medicament is prevented without the use of surfactants, protective colloids or cosolvents.

12 Claims, 3 Drawing Sheets

AEROSOL DRUG FORMULATIONS CONTAINING POLYGLYCOLYZED GLYCERIDES

The present invention relates to drug formulations for aerosol delivery which are compatible with non-chlorofluorocarbon propellants, and especially to excipients which are useful therein. In particular, the invention relates to inhalable formulations comprising polyglycolyzed glycerides, which formulations possess a variety of advantageous properties.

BACKGROUND OF THE INVENTION

Numerous pharmaceutical compounds are preferentially delivered by means of metered dose inhalation (MDI) devices, in which a physiologically inert propellant of high vapor pressure is used to discharge a precise amount of medication with each operation. These MDI devices, also known as aerosols or inhalers, have found widespread use among patients suffering, for example, from episodic or chronic asthma. The propellants of choice have historically been chlorofluoro-carbons, such Propellant 11 (trichlorofluoromethane), Propellant 12 (dichlorodifluoromethane) and Propellant 114 (dichlorotetrafluoroethane).

In recent years, however, there have been growing concerns that chlorofluorocarbon (CFC) propellants have detrimental environmental effects, and in particular that they interfere with the protective upper-atmosphere ozone layer. Under an international accord (the Montreal Protocol), the use of CFC propellants will be prohibited by the start of the year 2000, and possibly sooner. Alternative propellant vehicles are being developed which exhibit little or no ozone depletion potential (ODP). Such alternative propellants include two—HFC-134a (1,1,1,2-tetrafluoroethane) and HFC-227ea (1,1,1,2,3,3,3-heptafluoropropane)—which have negligible ODP and are currently undergoing safety and environmental testing.

Unfortunately, many surfactants which are generally used in known MDI formulations have been found to be imiscible, and therefore incompatible, with these new, non-CFC propellants. Such surfactants are necessary to prevent aggregation (in the form of "caking" or crystallization, for example) of the medicinally active compound in the reservoir of the inhaler, to facilitate uniform dosing upon aerosol administration, and to provide an aerosol spray discharge having a favorable respirable fraction (that is, a particle size distribution such that a large portion of the discharge reaches the alveoli where absorption takes place, and thus produces high lung deposition efficiencies). To overcome this incompatibility, it has previously been taught to include cosolvents (such as ethanol) with the non-CFC propellants so as to blend the surfactants into the formulation. Another suggested approach has been to emulsify the MDI formulation in the presence of a surfactant with low-vapor pressure additives, such as polyhydroxy alcohols as for example propylene glycol.

Such cosolvents or additives may of course be physiologically active, and in some instances may not be tolerated by the user of an MDI medication. There is therefore a need for MDI formulations compatible with non-CFC, non-ozone depleting propellants, which prevent aggregation of drug particles without the use of cosolvents or similar carrier additives, and which provide uniformity of dosing and a favorable respirable fraction.

Surprisingly, it has now been found that polyglycolyzed glycerides, as for example Labrafac® CM 6, Labrafil® WL 2609 BS, Labrafac® CM 8, Labrafac® CM 10, Labrafil® M 10, Labrafil® NA 10, Labrafac® CM 12, Labrasol® (Labrafac® CM 14) and the like are capable of stabilizing MDI formulations utilizing non-ozone depleting propellants such as HFC-134a and HFC-227ea so as to (i) prevent aggregation, (ii) provide dosing uniformity, and (iii) afford high lung deposition efficiency without the need for either surfactants or cosolvents. Additionally, the polyglycolyzed glycerides have the unexpected benefit of providing adequate lubrication for the valve used in an MDI product without the need for additional lubricants, thus aiding reliable functioning of the aerosol device throughout the life of the product.

Significant characteristics of such polyglycolyzed glycerides used are that: (i) they are non-ionic surface active agents which do not chemically interact with drug; (ii) they have been used previously in oral drug delivery liquid dosage form, thereby establishing their physiological acceptability; (iii) their hydrophilic lipophilic balance (HLB) values are much higher than sorbitan trioleate (SPAN 85), ranging in the case of Labrafac® from 6 to 14 and in the case of Labrafil® products of interest from 6 to 10 (compared to 4 for SPAN 85); and (iv) they are highly soluble in HFC 134a. Non-CFC formulations which include polyglycolyzed glycerides do not require the addition of (i) cosolvents like ethanol to blend the surfactant into the formulation, (ii) conventional surfactants such as sorbitan trioleate (SPAN 85), sorbitan monooleate and oleic acid, or (iii) protective colloids like sodium lauryl sulfate, cholesterol and palmitic acid, yet provide high lung deposition efficiencies and respirable fractions comparable to those obtained with known CFC-propellant formulations. It is thus expected that non-CFC formulations comprising polyglycolyzed glycerides will be useful for the delivery of both peptide and non-peptide pharmaceutical medicaments for which MDI delivery is deemed preferable.

BRIEF DESCRIPTION OF THE DRAWINGS

FIG. 1 illustrates the drug content uniformity of formulations of the present invention containing cyclosporin A (25 mg/mL) and Labrafac® in the propel/ant HFC-134a.

FIG. 2 illustrates dosimetry reproducibility of formulations of the present invention containing cyclosporin A (25 mg/mL) and Labrafac® (3 mg/mL) in the propellant HFC-134a.

SUMMARY OF THE INVENTION

According to one aspect of the present invention, pharmaceutical compositions are disclosed which are useful for aerosol delivery, as for example by inhalation and pulmonary absorption, comprising a therapeutically effective amount of a medicament, a non-chlorofluorocarbon propellant, and a polyglycolyzed glyceride such as Labrafac® CM 6, Labrafil® WL 2609 BS, Labrafac® CM 8, Labrafac® CM 10, Labrafil® M 10, Labrafil® NA10, Labrafac® CM 12 or Labrasol® (Labrafac® CM 14). The compositions may optionally comprise a sweetener such as Nutrasweet® (aspartame) an/or a taste-masking agent such as menthol. The propellants in such compositions are preferably fluorocarbons and, more preferably, non-ozone depleting fluorocarbons such as HFC-134a or HFC-227ea. The medicaments to be delivered are preferably LHRH analogs, 5-lipoxygenase inhibitors, immunosuppressants or bronchodilators; especially preferred medicaments include leuprolide acetate, the LHRH antagonist Ac-D-2-Nal-D-4-Cl-Phe-D-3-Pal-Ser-N-MeTyr-D-Lys(Nic)-leu-Lys(N-Isp)-Pro-D-Ala-NH$_2$ (hereinafter "D-2-Nal"), the 5-lipoxygenase inhibitor N-[3-[5-(4-fluorophenylmethyl)-2-thienyl]-1-methyl-2-propynyl]-N-hydroxyurea, the immunosuppressant cyclosporin A, and the adrenergic bronchodilators isoproterenol and albuterol. (As used herein, the terms "5-lipoxygenase inhibitor" or "5-LO inhibitor" refer to any physiologically active compound capable of affecting leukotriene biosynthesis.)

The polyglycolyzed glycerides used in the present invention may be present in a concentration of between about 0.001% and about 10% by weight, preferably in a concentration of between about 0.002% and about 5% by weight and more preferably in a concentration of between 0.01% and about 1%.

A sweetener such as aspartame and/or a taste-masking agent such as menthol may also be present in concentrations of between about 0.0001% and about 10% each by weight.

Particularly preferred pharmaceutical compositions embodying the present invention include those comprising leuprolide acetate in a concentration of between 0.05% and 5% by weight, Labrafac® in a concentration of between 0.01% and 1% by weight, aspartame in a concentration of between 0.02% and 0.5% by weight, and menthol in a concentration of between 0.01 and 0.25% by weight.

Especially preferred pharmaceutical compositions embodying the present invention are those comprising leuprolide acetate in a concentration of between 0.125% and 0.5% by weight, Labrafac® in a concentration of between 0.1% and 0.5% by weight, aspartame in a concentration of between 0.05% and 0.2% by weight, and menthol in a concentration of between 0.025 and 0.1% by weight.

Alternative, especially preferred pharmaceutical compositions embodying the present invention are those comprising leuprolide acetate in a concentration of between 0.5% and 2% by weight, Labrafac® in a concentration of between 0.2% and 1% by weight, aspartame in a concentration of about 0.1% by weight, and menthol in a concentration of about 0.05% by weight.

In a further aspect of the present invention is disclosed a method of preparing a stable suspension of particles of a medicament in a liquid phase non-chlorofluorocarbon aerosol propellant, which method comprises (a) combining the medicament, the propellant, and a polyglycolyzed glyceride in an amount sufficient to prevent aggregation of the particles to form a mixture and (b) agitating the mixture to completely blend the various components. (The order of addition may alternatively be varied so that the medicament and the polyglycolized glyceride, or the propellant and the polyglycolized glyceride, or the medicament and the propellant are first mixed prior to addition of the third component.) Preferably, the polyglycolyzed glyceride may be added in an amount of between about 0.001% and about 5% by weight; more preferably, the polyglycolyzed glyceride may be added in an amount of between about 0.01% and about 1% by weight. The propellants, medicaments and polyglycolyzed glycerides suitable for use in the method of the present invention are those described above in connection with the pharmaceutical compositions of this invention.

DETAILED DESCRIPTION OF THE INVENTION

It is expected that numerous non-ozone depleting aerosol propellants may be used with the compositions and methods of the present invention. These include not only HFC-134a and HFC-27ea, described above, but also halogenated alkanes in general, such as HCFC-123 (1,1,1-trifluoro-2,2-dichloroethane), HCFC-124 (1,1,1,2-tetrafluorochloroethane), HCFC-141b, HCFC-225, HFC-125, FC-C51-12 (perfluorodimethylcyclobutane), DYMEL A (dimethyl ether) and DYMEL 152a (1,1-difluoroethane). The preferred propellants are HFC-134a and HFC-27ea, HFC-134a being especially preferred.

The term "polyglycolyzed glyceride" as used herein refers to specific mixtures of mono, di and triglycerides and polyethylene glycol mono and diesters, obtained either by partial alcoholysis of hydrogenated vegetable oils using polyethylene glycol of relative molecular weight ranging from about 200 to about 2000, or by esterification of fatty acids using polyethylene glycol of relative molecular weight ranging from about 200 to about 2000 and glycerol. The polyglycolyzed glycerides of the present invention have Hydrophilic Lipophilic Balance (HLB) values of between and including 6 and 14. The free glycerol content is less than 3%. Examples of suitable polyglycolyzed glycerides include Labrafac® CM 6, Labrafil® WL 2609 BS, Labrafac® CM 8, Labrafac® CM 10, Labrafil® M 10, Labrafil® NA10, Labrafac® CM 12, Labrasol® (Labrafac® CM 14) and the like.

Examples of polyglycolyzed glycerides include Labrafac® CM 6, Labrafil® WL 2609 BS, Labrafac® CM 8, Labrafac® CM 10, Labrafil® M 10, Labrafil® NA10, Labrafac® CM 12, and Labrasol® (Labrafac® CM 14). Preferred polyglycolyzed glycerides having HLB values of between 6 and 14, inclusive, and containing medium chain ($C_8$–$C_{10}$) triglycerides, are Labrafac® CM 6, Labrafac® CM 8, Labrafac® CM 10, Labrafac® CM 12, and Labrasol® (Labrafac® CM 14). Of these, especially preferred and regarded as the best mode of carrying out the present invention is the polyglycolyzed glyceride Labrafac® CM 10.

It is also expected that analogs and derivatives of the above polyglycolyzed glycerides will be identified which are suitable for use in the compositions and methods of the present invention. To the extent that these analogs and derivatives are similar in structure to or are readily obtained by chemical modification of the polyglycolyzed glycerides, while substantially retaining the physical properties of the polyglycolyzed glycerides, such analogs and derivatives are intended to be included among the compositions and methods of the present invention.

It is expected that the compositions and methods of the invention will be suitable for the administration of a wide variety of peptide and non-peptide drugs. Examples of peptides which may be delivered in this fashion are interferons and other macrophage activation factors, such as lymphokines, muramyl dipeptide (MDP), γ-interferon, and interferons a and b, and related antiviral and tumoricidal agents; opioid peptides and neuropeptides, such as enkaphalins, endorphins and dynorphins, and related analgesics; renin inhibitors including new-generation antihypertensive agents; cholecystokinins (CCK analogs) such as CCK, ceruletide and eledoisin, and related cardiovascular- and CNS-targeting agents; leukotrienes and prostaglandins, such as oxytocin, and related antiinflammatory, oxytocic and abortifacient compounds; erythropoietin and analogs thereof, as well as related haematinics; LHRH analogs, such as leuprolide, buserelin and nafarelin, and related down-regulators of pituitary receptors; parathyroid hormone and other growth hormone analogs; enzymes, such as DNase, catalase and alpha-1 antitrypsin;

immunosuppressants such as cyclosporin; GM-CSF and other immunomodulators; and insulin. Such peptides or peptide analogs are frequently not well-absorbed when given orally. A preferred medicament for use in the formulations of the present invention is leuprolide acetate.

Examples of non-peptides which may readily be delivered using the compositions and methods of the present invention are beta-agonists, such as isoproterenol, albuterol, isoetherine and metoproteronol, and related anti-asthmatics; steroids, such as flunisolide, and similar anti-asthmatics; cholinergic agents, such as cromolyn, and related anti-asthmatics; and 5-lipoxygenase inhibitors, such as zileuton and the hydroxyurea compound described above, and related leukotriene inhibitors. Such non-peptides may lend themselves to oral administration, but when given by inhalation are found to produce rapid reversal of bronchoconstriction in cases of allergic airway disease and asthma. Also, these compounds may be administered more frequently as MDI formulations than when given orally.

The medicaments useful in the compositions of the present invention include not only those specifically named above, but also where appropriate the pharmaceutically acceptable salts, esters, amides and prodrugs thereof. By "pharmaceutically acceptable salts, esters, amides and prodrugs" is meant those carboxylate salts, amino acid addition salts, esters, amides and prodrugs of a compound which are, within the scope of sound medical judgement, suitable for use in contact with the tissues of humans and lower animals with undue toxicity, irritation, allergic response and the like, commensurate with a reasonable benefit/risk ratio and effective for their intended use. In particular, the term "salts" refers to the relatively non-toxic, inorganic and organic acid addition salts of a medicinal compound. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66:1–19 (1977), incorporated herein by reference.)

Examples of pharmaceutically acceptable, non-toxic esters of a compound include ($C_1$-to-$C_6$ alkyl) esters wherein the alkyl group is a straight or branched chain. Acceptable esters also include ($C_5$-to-$C_7$ cycloalkyl) esters as well as arylalkyl esters such as, but not limited to, benzyl; ($C_1$-to-$C_4$ alkyl) esters are preferred.

Examples of pharmaceutically acceptable, non-toxic amides of medicinal compounds include amides derived from ammonia, primary ($C_1$-to-$C_6$ alkyl) amines and secondary ($C_1$-to-$C_6$ dialkyl) amines wherein the alkyl groups are straight or branched chain. In the case of secondary amines the amine may also be in the form of a 5- or 6-membered heterocycle containing one nitrogen atom. Amides derived from ammonia, ($C_1$-to-$C_3$ alkyl) primary amides and ($C_1$-to-$C_2$ dialkyl) secondary amides are preferred. Amides of the compounds of the invention may be prepared according to conventional methods.

The term "prodrug" refers to compounds that are rapidly transformed in vivo to yield the parent medicinal compound, as for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press (1987), both of which are incorporated herein by reference.

When used in the above compositions, a therapeutically effective amount of a medicament of the present invention may be employed in pure form or, where such forms exist, in pharmaceutically acceptable salt, ester or prodrug form. By a "therapeutically effective amount" of a medicament is meant a sufficient amount of the compound to obtain the intended therapeutic benefit, at a reasonable benefit/risk ratio applicable to any medical treatment. It will be understood, however, that the total daily usage of the medicaments and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses at levels lower than required to achieve the desired therapeutic effect and to gradually increase the dosage until the desired effect is achieved.

The total daily doses of the medicaments contemplated for use with this invention, and consequently the concentrations by weight of the medicaments in the respective compositions, may vary widely. In the case of an LHRH analog, such as leuprolide acetate, the intended daily dose may range from about 0.01 to about 5 mg/day; accordingly, where an aerosol inhaler is to be used several times a day with a discharge volume of between about 5 and about 250 µL, the concentration of medicament will be between about 0.2 and about 20 mg/mL. Similarly, in the case of a 5-lipoxygenase inhibitor expected to be administered in a daily dose ranging from about 0.01 to about 10 mg/kg/day, the concentration will be between about 0.001 and about 100 mg/mL. Of course, medicament concentrations outside of these ranges may also be suitable, where different potencies, dosing frequencies and discharge volumes are used.

The compositions of the invention may be prepared by combining the polyglycolyzed glyceride with a medicament which has been milled or otherwise reduced to a desired particle size, and placing the mixture in a suitable aerosol container or vial. After sealing the container, an aerosol propellant is introduced and the system is agitated to fully blend the ingredients. Alternatively, the polyglycolyzed glyceride and medicament may be milled together, either before or after addition of propellant. In some instances, it may be necessary to wet-mill the medicament in a closed system, as for example under temperature and pressure conditions which permit the medicament to be milled while mixed with a liquid-phase aerosol propellant. It is expected that, for any particular combination of medicament, propellant and polyglycolyzed glycerides, the ideal order of addition of ingredients and the conditions under which they are to be combined may readily be determined.

The compositions and methods of the present invention will be better understood in connection with the following examples, which are intended as an illustration of and not a limitation upon the scope of the invention. Both below and throughout the specification, it is intended that citations to the available literature are expressly incorporated by reference.

EXAMPLE 1

Characterization of Labrafac® CM 10

Labrafac® CM 10 comprises medium chain ($C_{8-C10}$) polyglycolyzed glycerides, and has a Hydrophilic Lipophilic Balance value of about 10. It is an oily liquid with a hint odor and a color on the Gardner Scale of <5. Specific gravity at 20° C. is 1.000–1.040. Refractive Index at 20° C. is 1.430–1.485. Viscosity at 20° C. (mPa.s) is 20–90. Solubility at 20° C.: (95% in $H_2O$), very soluble; chloroform, very soluble; methylene chloride, very soluble; water, dispersible; mineral oil, insoluble; vegetable oil, very soluble. Chemical characteristics: Acid Value (mg KOH/g), <2.00; Saponification Value (mg KOH/g), 160–200; Iodine Value (g $I_2$/100 g), <2; Hydroxyl Value (mg KOH/g), 115–155; Peroxide Value (meq $O_2$/kg), <12.5; Alkaline Impurities (ppm MaOH), <80; Water Content (%), <1.00; Free Glycerol Content (%), <3.0; 1 Monoglycerides Content (%), <15.0; Sulphated Ashes (%), <0.10; Heavy Metals (ppm Pb), <10.

EXAMPLE 2 physical Stability of MDI Formulations Containing Labrafac®

A determination of the effect of Labrafac® CM 10 on the physical stability of several MDI formulations prepared with HFA-134a was conducted as follows: Labrafac® CM 10 (Gattefossé, Westwood, N.J.) and each of the drugs being formulated were combined in the amounts shown in appropriate transparent aerosol containers (vials). (Leuprolide acetate and its preparation are described in United States Patent No. 4,005,063, issued Jan. 25, 1977, which is incorporated herein by reference.) Additionally, to some of the vials was added the sweetener aspartame (Nutrasweet Corp., Skokie, Ill.) in an amount to produce a final concentration of 0.2% by weight. The vials were crimped and charged with approximately 10 mL of HFC-134a and agitated to blend the ingredients. The dispersion quality in each preparation was evaluated visually after 24 hours using the following criteria:

Poor: Phase separation; top phase clear, bottom phase containing solids

Fair: Partial phase separation; cloudiness in the top phase

Good: Grainy appearance; no phase separation

Excellent: Milky homogeneous appearance; no phase separation

Results of these tests are shown below in Tables 1 and 2. The data obtained show that the formulations of the present invention maintain a high degree of dispersion even after 24 hours. By comparison, control formulations of each of the test compounds (which were prepared without polyglycolyzed glyceride) are seen to have unacceptable dispersion quality (which was evident in each case after less than 30 seconds).

TABLE 1

Dispersion Quality of Leuprolide Acetate in HFA-134a

| Leuprolide Concentration | Labrafac® CM 10 Concentration | Aspartame Concentration | Dispersion Quality (24 Hours) |
|---|---|---|---|
| 1% | 0.05% | 0.00% | Good |
| 1% | 0.10% | 0.00% | Good |
| 1% | 0.30% | 0.00% | Good |
| 1% | 0.50% | 0.00% | Good |
| 1% | 0.20% | 0.01% | Good |
| 1% | 0.20% | 0.05% | Good |
| 1% | 0.20% | 0.10% | Good |
| 1% | 0.20% | 0.20% | Good |

TABLE 2

Dispersion Quality of Cyclosporin A in HFA-134a

| Cyclosporin A Concentration | Labrafac® CM 10 Concentration | Dispersion Quality (24 Hours) |
|---|---|---|
| 2.5% | 0.00% | Poor |
| 2.5% | 0.05% | Good |
| 2.5% | 0.10% | Good |
| 2.5% | 0.15% | Good |
| 2.5% | 0.25% | Good |

A further comparison of various dispersants was conducted as before. The results, shown in Table 3, demonstrate that dispersion quality of the formulation of the present invention, after 24 hours, is superior to that obtained using other known dispersants.

TABLE 3

Dispersion Quality of 25 mg/mL Cyclosporin A in HFA-134a

| Sample No. | Dispersant 2.5 mg/mL | Dispersion Quality (24 Hours) |
|---|---|---|
| 1 | Span 85 | Poor |
| 2 | Oleic Acid | Poor |
| 3 | Lecithin | Fair |
| 4 | Span 20 | Poor |
| 5 | Decanesulfonic Acid | Good |
| 6 | Sodium Lauryl Sulfate | Good |
| 7 | Cholesterol | Good |
| 8 | Vitamin E | Good |
| 9 | Labrafac | Excellent |
| 10 | Ascorbic Acid | Good |

EXAMPLE 3

Preparation of MDI Formulations for Performance Testing

For each test formulation, between 7 and 12 g of glass beads were placed into a suitable glass aerosol container (vial), along with 100 mg to 250 mg drug, Labrafac® CM 10 and Aspartame in the amounts needed to produce the desired final concentrations. The vials were crimped shut with valves having delivery values (volumes per spray) of either 50 μL or 100 μL, and then charged with 10 mL of HFA-134a propellant. The filled vials were then shaken for 24 hours to mill and disperse the drug, after which testing was carried out in vitro or in vivo as described below.

EXAMPLE 4

Uniformity of MDI Delivery of Compositions Containing Leuprolide

Delivery uniformity and physical stability of the compositions of the invention containing the Leuprolide were tested as follows: Each vial was shaken and its valve primed by aerosolizing 5 times in succession, after which the vial was weighed. The valve of each vial was then actuated ten times, followed by another weighing. This process was repeated until shot weights had been determined for 100 sprays.

The shot weight data, shown below in Table 4, demonstrate the uniformity with which the compositions of the present invention are delivered by a MDI device.

TABLE 4

Shot Weight Data for Leuprolide Aerosol (10 mg/mL) Containing 0.2% Labrafac ® CM 10 and 0.05% Aspartame

| Sprays | Total Can 1 (grams) | Total Can 2 (grams) |
|---|---|---|
| 1–10 | 0.61 | 0.61 |
| 11–20 | 0.60 | 0.62 |
| 21–30 | 0.61 | 0.61 |
| 31–40 | 0.60 | 0.62 |
| 41–50 | 0.64 | 0.63 |
| 51–60 | 0.62 | 0.59 |
| 61–70 | 0.63 | 0.61 |
| 71–80 | 0.61 | 0.61 |
| 81–90 | 0.60 | 0.61 |
| 91–100 | 0.60 | 0.62 |

EXAMPLE 5

Uniformity of MDI Delivery of Compositions Containing Cyclosporin A

Delivery uniformity and physical stability of the compositions of the present invention containing cyclosporin A were tested as follows: Cyclosporin A was formulated as described above to produce a composition containing 25 mg/ml cyclosporin and either 3 or 5 mg/ml Labrafac® CM 10 as shown. Each vial was shaken and its valve (delivering 0.1 ml per spray) was primed by aerosolizing 5 times in succession, after which the vial was weighed. The valve of each vial was then actuated ten times, followed by another weighing. This process was repeated until shot weights had been determined for 70 sprays.

Figure 1:
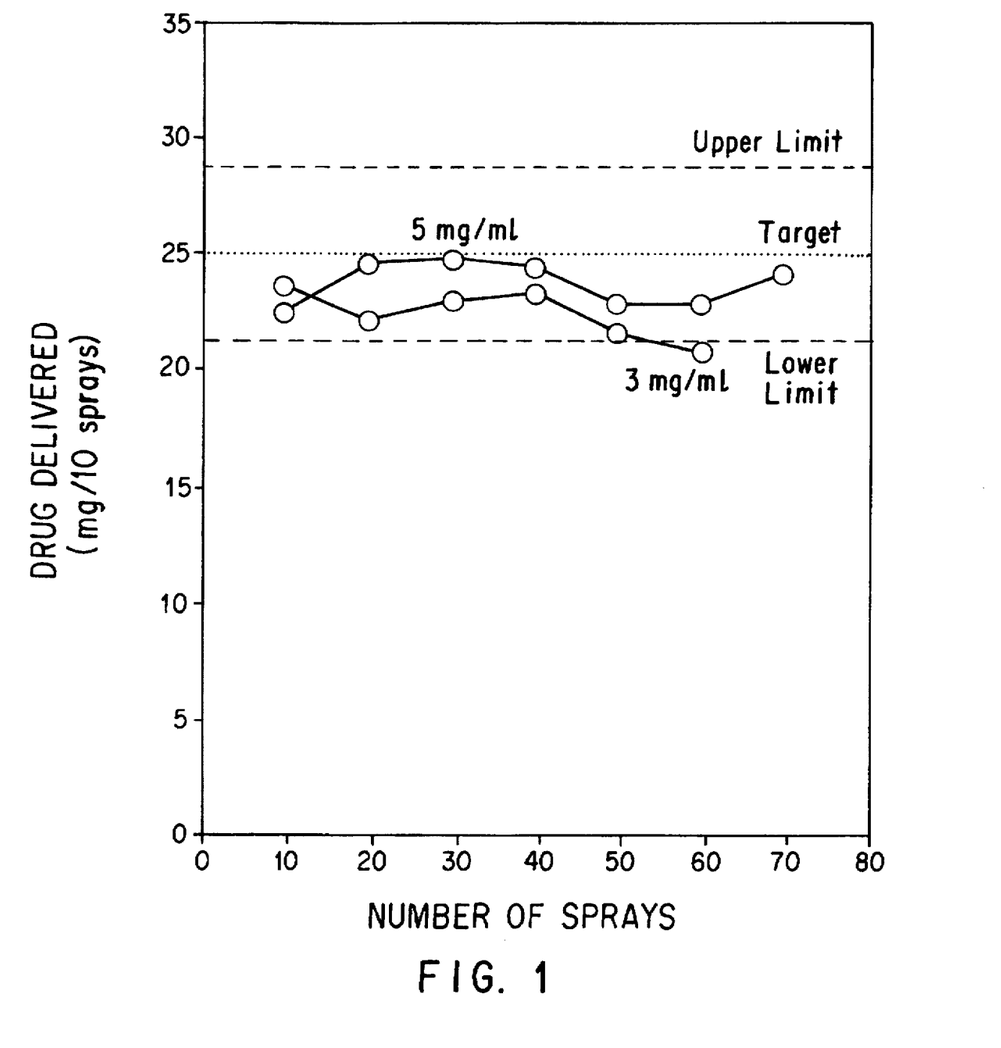

The drug content uniformity, shown in FIG. 1, shows the amount of drug delivered as mg per 10 sprays plotted against the number of sprays. These results demonstrate the uniformity with which the compositions of the present invention are delivered by a MDI device, in that all values through 45 sprays fall within the desired target range. Only after 45 sprays (that is, during "tail-off") do the values fall below the lower target.

EXAMPLE 6

Dosimetry Reproducibility of Compositions Containing Cyclosporin A

Dosimetry reproducibility of the compositions of the present invention containing Cyclosporin A were tested as follows: Cyclosporin A was formulated as described above to produce a composition containing 25 mg/ml cyclosporin and 3 mg/ml Labrafac® CM 10 in HFC-134a. Each vial was shaken and its valve (delivering 0.1 ml per spray) was primed by aerosolizing 5 times in succession. Then, on Day 0, the valve of each vial was submerged in a beaker of methanol and actuated five times, after which the amount of drug delivered was assayed using quantitative HPLC. This process was repeated on Days 3, 7, 10 and 12 for each vial.

Figure 2:
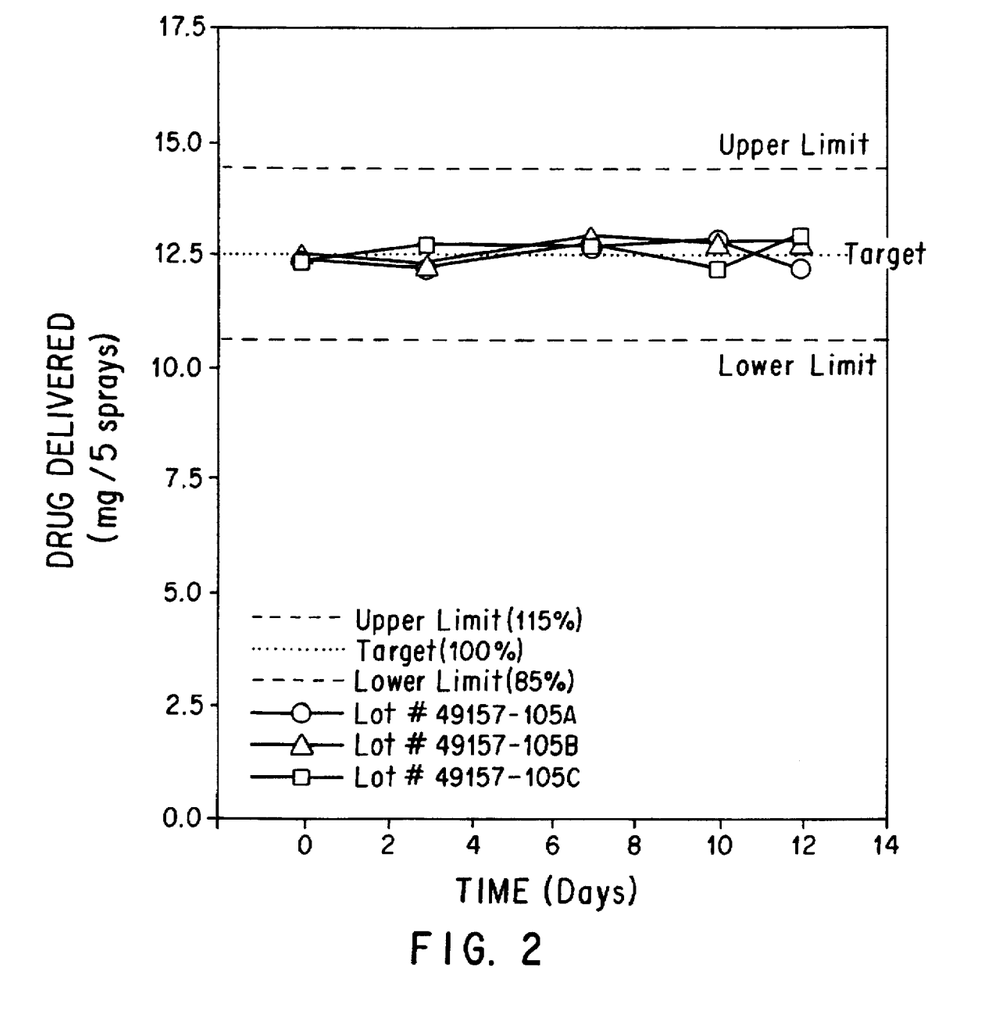

The results, shown in FIG. 2, shows the amount of drug delivered on each of the sampling dates for each of three test formulations. These results demonstrate a right correlation with the target dose, and demonstrate excellent dose reproducibility achieved by the present invention.

EXAMPLE 7

Bioavailability of MDI Compositions Containing Labrafac®

Using a test preparation of leuprolide containing 10 mg/mL drug, 0.2% (by weight) Labrafac® CM 10 and 0.05% (by weight) aspartame in HFC 134a propellant, bioavailability of aerosol-delivered drug was compared to that of an aqueous control formulation delivered intravenously (IV) and a CFC formula containing 0.5% sorbitan trioleate (SPAN 85, NDA commercial grade). Three or four tracheostomized beagle dogs (two-year-old females, Marshall Labs) were used for each group. To the dogs in the IV group, 0.1 mg/kg drug was given intravenously over a 1 minute period as a 1 mg/mL solution in 60% PEG 400 (polyethylene glycol, Union Carbide Co., Institute, W.Va.) in water. To the dogs in the aerosol groups, 0.3 mg/kg of drug was administered by sprays of the test formulations delivered into the trachea. Blood samples were collected at specified time intervals and analyzed for drug concentration using high performance liquid chromatography.

The results of these studies, shown below in Table 5, demonstrate that drugs are effectively administered using the MDI formulations of the present invention. In particular, bioavailability of the aerosolized drug over a 24-hour period was a ~95% that of the same amount delivered intravenously, based on area-under-curve (AUC) calculations. Net bioavailability, when corrected for non-absorptive loss of drug (as for example due to loss in the dosing device, inertial impaction of the spray in the trachea, and expulsion with exhaled air), exceeded 90% of that obtained using intravenous administration.

TABLE 5

Comparison of Intravenous and MDI Delivery of Leuprolide

| Formula | Dose of Leuprolide | No. of Dogs | AUC (CV) min (ng/mL) | Bioavailability (%) |
|---|---|---|---|---|
| IV | 0.1 mg/kg | 3 | 17651 (0.2) | 100 |
| CFC | 0.3 mg/kg | 4 | 45693 (0.4) | 81 |
| HFC | 0.3 mg/kg | 4 | 50479 (0.4) | 93 |

CFC Formula: 0.5% SPAN 85
HFC Formula: 0.2% Labrafac ® CM 10, 0.05% aspartame

EXAMPLE 8

Respirable Fraction of Leuprolide MDI Compositions Containing Labrafac®

Particle sizing was done by light scattering using a method based on the Fraunhoffer optical diffraction principle. Particle size data on reference standard dispersions were collected by sweeping a total of two hundred times to insure that a representative, randomly oriented sample from all size classes had been measured. Samples prepared as aerosolized spray were measured for reference standards and formulations of multiple lots of leuprolide and dextrose. For all samples, the log-normal model was used for analyzing the distribution.

Respirable fraction (RF) measurements were made from the particle size distribution data. The term refers to the fraction of drug estimated from biophysical measurements to deposit in the peripheral zones of the lung. The respirable fraction is the amount of drug in mg which is less than 4.7 μm in diameter divided by the total amount of drug sprayed in mg; this fraction is multiplied by 100 to give the RF as a percentage.

Figure 3:
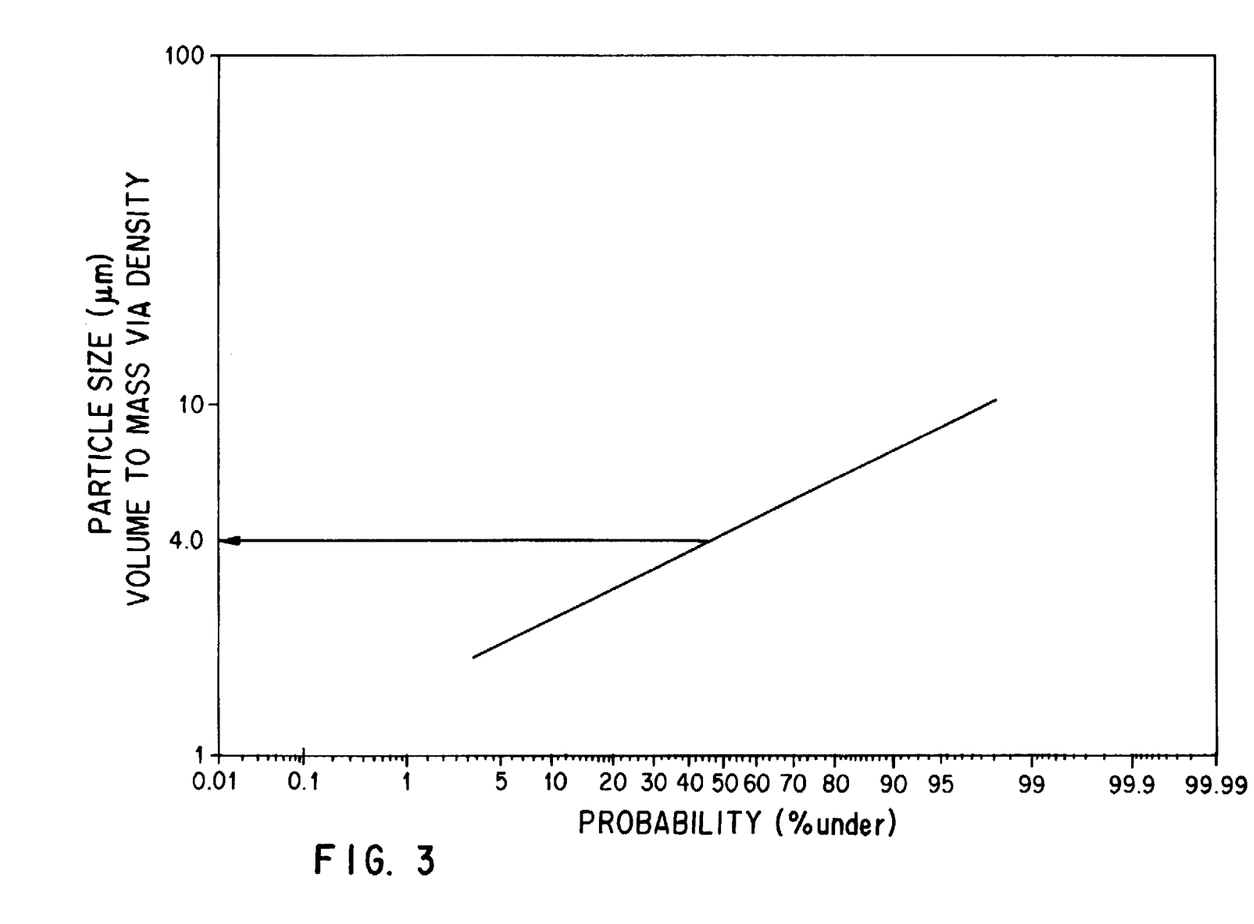
FIG. 3 illustrates particle size distribution obtained using a formulation of the present invention containing leuprolide (10 mg/mL) and 0.2% Labrafac® CM 10 and 0.05% aspartame.

The test formulation was a leuprolide aerosol with a concentration of 10 mg/mL containing 0.2% (by weight) Labrafac® CM 10 and 0.05% (by weight) aspartame. The particle size was plotted against the percentage at or below a given particle size. The results are shown in FIG. 3. A favorable respirable fraction has a particle size distribution such that a large portion of the discharge reaches the alveoli where absorption takes place, and thus producing high lung deposition efficiencies; the ideal respirable range is between 0.5 μm and 4.7 μm. The data show that 55% of the formulation falls within the respirable range; this can be compared with many formulations of the prior art which have only 25% failing within the range.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the substituents, means of preparation and/or methods of use of the invention, may be made without departing from the spirit and scope thereof.

What is claimed is:

1. A pharmaceutical composition for aerosol delivery consisting essentially of a medicament, a non-chlorofluorocarbon propellant as the sole propellant, and a polyglycolized glyceride having a hydrophilic lipophilic balance of between and including 6 and 14, wherein the medicament is present in a concentration of between about 0.05% and about 5% by weight and the polyglycolized glyceride is present in a concentration of between about 0.001% and about 10% by weight, the non-chlorofluorocarbon propellant is selected from the group consisting of HCFC 123, HCFC 124, HCFC 141b, HCFC 225, HCFC 125, perfluorodimethylcyclobutane DYMEL A, DYMEL 152a, HFC 134a and HFC 227ea, provided said composition does not contain a surfactant, protective colloid or cosolvent.

2. A pharmaceutical composition according to claim 1 wherein the propellant is selected from the group consisting of HFC-134a and HFC-227ea.

3. A pharmaceutical composition according to claim 1 wherein the polyglycolyzed glyceride is present in a concentration of between about 0.002% and about 5% by weight.

4. A pharmaceutical composition according to claim 1 wherein the polyglycolyzed glyceride is present in a concentration of between about 0.01% and about 1% by weight.

5. A pharmaceutical composition according to claim 2 wherein the medicament is selected from the group consisting of LHRH analogs, 5-lipoxygenase inhibitors, immunosuppressants and bronchodilators.

6. A pharmaceutical composition according to claim 1 wherein the medicament is selected from the group consisting of leuprolide acetate, Ac-D-2-Nal-D-4-ClPhe-D-3-Pal-Ser-N-MeTyr-D-Lys(Nic)-Leu-Lys(N-Isp)-Pro-D-Ala-NH$_2$; cyclosporin A; albuterol and isoproterenol.

7. A pharmaceutical composition according to claim 3 wherein the medicament is leuprolide acetate.

8. A pharmaceutical composition according to claim 5 wherein the propellant is HFC-134a.

9. A pharmaceutical composition according to claim 7 wherein the polyglycolyzed glyceride is present in a concentration of between about 0.01% and about 1% by weight.

10. A pharmaceutical composition according to claim 6 comprising leuprolide acetate in a concentration of between about 0.05% and about 5% by weight, polyglycolyzed glyceride in a concentration of between about 0.01% and about 1% by weight, aspartame in a concentration of between about 0.05% and 0.2% by weight, and menthol in a concentration of between about 0.025% and about 0.1% by weight, wherein said polyglycolized glyceride is a saturated polyglycolized $C_8$–$C_{10}$ glyceride having a Hydrophilic Lipophilic Balance of 10; an acid value (mg KOH/g) of <2; a saponification value (mg KOH/g) of 160–200; an iodine value (g $I_2$/100 g) of <2; a hydroxyl value (mg KOH/g) of 115–155; a peroxide value (meq $O_2$/kg) of <12.5; alkaline impurities (ppm NaOH) of <80; a water content of <1%; free glycerol content of <3%; and a monoglycerides content of <15%.

11. A pharmaceutical composition according to claim 10 comprising leuprolide acetate in a concentration of between about 0.125% and about 0.5% by weight, polyglycolyzed glyceride in a concentration of between about 0.1% and about 0.5% by weight, aspartame in a concentration of between about 0.05% and 0.2% by weight, and menthol in a concentration of between about 0.025% and about 0.1% by weight.

12. A pharmaceutical composition according to claim 10 comprising leuprolide acetate in a concentration of between about 0.5% and about 2% by weight, polyglycolyzed glyceride in a concentration of between about 0.2% and about 1% by weight, aspartame in a concentration of about 0.1% by weight, and menthol in a concentration of about 0.05% by weight.

* * * * *

UNITED STATES PATENT AND TRADEMARK OFFICE
CERTIFICATE OF CORRECTION

PATENT NO. : 5,635,159
DATED : June 3, 1997
INVENTOR(S) : Fu Lu et al.

It is certified that error appears in the above-indentified patent and that said Letters Patent is hereby corrected as shown below:

In the abstract, line 9, change "nonchlorofluorocarbon" to --non-chlorofluorocarbon--.

Column 3, line 4, change "leu" to --Leu--.

Signed and Sealed this

Twenty-sixth Day of August, 1997

Attest:

BRUCE LEHMAN

Attesting Officer      Commissioner of Patents and Trademarks